US005582996A

United States Patent [19]

Curtis

[11] Patent Number: 5,582,996
[45] Date of Patent: Dec. 10, 1996

[54] BIFUNCTIONAL ANTIBODIES AND METHOD OF PREPARING SAME

[75] Inventor: Peter J. Curtis, Philadelphia, Pa.

[73] Assignee: The Wistar Institute of Anatomy & Biology, Philadelphia, Pa.

[21] Appl. No.: 250,656

[22] Filed: May 27, 1994

Related U.S. Application Data

[63] Continuation of Ser. No. 917,074, filed as PCT/US91/09019, Dec. 3, 1991 published as WO92/10209, Jun. 25, 1992, abandoned, which is a continuation-in-part of Ser. No. 622,983, Dec. 4, 1990, abandoned.

[51] Int. Cl.$^6$ ............. C12P 21/08; C07K 16/00; C07K 16/46; G01N 33/53
[52] U.S. Cl. ............. 435/7.1; 530/387.3; 530/391.3; 435/7.9; 435/69.6; 435/69.7; 436/542
[58] Field of Search ............. 530/387.3, 391.3; 435/7.1, 69.7, 69.6; 436/542

[56] References Cited

U.S. PATENT DOCUMENTS 4,714,681  12/1987  Reading ............. 430/240.27

FOREIGN PATENT DOCUMENTS

| 2019559 | 12/1990 | Canada . |
| 0369566 | 5/1990 | European Pat. Off. . |
| 0468637 | 1/1992 | European Pat. Off. . |
| WO91/05805 | 5/1991 | WIPO . |
| WO91/05856 | 5/1991 | WIPO . |
| WO91/05871 | 5/1991 | WIPO . |
| WO92/10209 | 6/1992 | WIPO . |
| WO93/11162 | 6/1993 | WIPO . |

OTHER PUBLICATIONS

Sueng Von et al. PNAS. vol. 87 5322–5326 1990 (For interest only).
Burgess et. al. The Journal of Cell Biology Nov. 1990 vol. 111, 2129.
Lazar et. al. Molecular and Cellular Biology Mar. 1988, 1247.
Tao et. al. Journal of Immunology vol. 143 1989 p. 2595.
Glennie et. al. Journal of Immunology. vol. 141, 3662– 1988 (for interest only).
Milstein and Cuello, Nature, 305:537–540 (1983).
Staerz et al, Nature, 314:628–631 (1985) [Staerz I].
Perez et al, Nature, 316:354–356 (1985).
Staerz and Bevan, Proc. Natl. Acad. Sci. USA, 83:1453–1457 (1986) [Staerz II].
Clark and Waldmann, JNCI, 79:1393–1401 (1987).
Gilliland et al, Proc. Natl. Acad. Sci. USA, 85:7719–7723 (1988).
Staerz et al, Eur. J. Immunol., 17:571–574 (1987) [Staerz III].
Haber et al, Science, 243:51–56 (1989).
DeMonte et al, Proc. Natl. Acad. Sci., USA, 87:2941–2945 (1990).
Lenz and Weidle, Gene, 87:213–218 (1990).
Gentz et al, Science, 243:1695–1699 (1989).
W. D. Huse et al, Science, 246:1275–1281 (1989).
Williams, Trends in Biotech., 6:36–42 (1988).
S. Shin and S. L. Morrison, Proc. Natl. Acad. Sci. USA, 87:5322–5326 (1990).
S. A. Kostelny et al, J. Immunol., 148(5):1547–1553 (1992).
P. Pack and A. Pluckthun, Biochemistry, 31(6):1579–1584 (1992).
T. Nitta et al, Lancet, 335:368–371 (1990).
P. Curtis, "Novel Approach to the Construction of Bispecific Antibodies", Abstract, 7th International Conference on Monoclonal Antibody Immunoconjugates for Cancer, San Diego, Mar. 5–7, 1992.
E. O'Shea et al, "Preferential Heterodimer Formation by Isolated Leucine Zippers from Fos and Jun", *Science*, 245:646–648 (1989).
L. Ransone et al, "Fos–Jun Interaction: Mutational Analysis of the Leucine Zipper Domain of Both Proteins", *Genes & Development*, 3:770–781 (Jun. 10, 1989).
J. Sellers et al, "Chaning Fos Oncoprotein to a Jun–Independent DNA–Binding Protein with GCN4 Dimerization Specificity by Swapping 'Leucine Zippers'", *Nature*, 341:74–76 (Sep. 7, 1989).
T. Abel et al, "Action of Leucine Zippers", *Nature*, 341:24–25 (Sep. 7, 1989).
C. Milstein et al, "Hybrid Hybridomas and the Production of Bi-Specific Monoclonal Antibodies", *Immunology Today*, 5(10):229–304 (Oct., 1984).
S. Busch et al, "Dimers, Leucine Zippers and DNA–binding Domains", *Trends Genet.*, 6(2):36–40 (Feb. 1990).
V. Chaudhary et al, "A Recombinant Immunotoxin Consisting of Two Antibody Variable Domains Fused to Pseudomonas exotoxin", *Nature*, 339:394–397 (Jun. 1, 1989).
M. Neuberger et al, "Recombinant Antibodies Possessing Novel Effector Functions", *Nature*, 312:604–608 (Dec. 13, 1984).
G. Williams et al, "Production of Antibody–Tagged Enzymes by Myeloma Cells: Application to DNA Polymerase I Klenow Fragment", *Gene*, 43:319–324 (1986).
J. Schnee et al, "Construction and Expression of a Recombinant Antibody–Targeted Plasminogen Activator", *Proc. Natl. Acad. Sci. USA*, 84:6904–6908 (Oct. 1987).
E. O'Shea et al, "Mechanism of Specificity in the Fos–Jun Oncoprotein Heterodimer", *Cell*, 68:699–708 (Feb. 21, 1992).
E. O'Shea et al, "X–ray Structure of the GCN4 Leucine Zipper, a Two–Stranded, Parallel Coiled Coil", *Science*, 254:539–544 (Oct. 25, 1991).
C. Vinson et al, "Dimerization Specificity of the Leucine Zipper–Containing bZIP Motif on DNA Binding: Prediction and Rational Design", *Genes and Development*, 7:1047–1058 (Jun. 4, 1993).
Landschultz et al. Science vol. 240 p. 1759 1988.

*Primary Examiner*—Lila Feisee
*Attorney, Agent, or Firm*—Howson and Howson

[57] ABSTRACT

A recombinant antibody capable of binding to two different antigenic sites, contains Fab fragments from the same or, preferably, different antibodies, which are brought into association by complementary interactive domains which have been inserted into a region of the antibody heavy chain constant region.

11 Claims, No Drawings

BIFUNCTIONAL ANTIBODIES AND METHOD OF PREPARING SAME

This is a file wrapper continuation of U.S. patent application Ser. No. 07/917,074, filed as PCT/US91/09019, Dec. 3, 1991 published as WO92/10209, Jun. 25, 1992 now abandoned, which is a continuation-in-part of U.S. patent application Ser. No. 07/622,983, filed Dec. 4, 1990, now abandoned.

This invention has been made with the financial assistance of a grant from the National Institutes of Health., Grant Number CA 40205.

This invention relates generally to the field of antibodies and more specifically to the field of bifunctional antibodies which have the ability to bind to two different antigens.

BACKGROUND OF THE INVENTION

Naturally occurring antibodies and monoclonal antibodies have two antigen binding sites which recognize the same antigen. In contrast, bifunctional antibodies, also referred to as heterobispecific antibodies, are synthetically or genetically engineered molecules that are capable of binding to two antigenic determinants. The ability to bind to the two different antigens resides in one molecule.

Bifunctional antibodies were first produced by fusing two different monoclonal antibody-producing hybridomas, which each recognized a different antigenic sites. According to this method each hybridoma is characterized by a different selectable marker, sensitivity to hypoxanthine-aminopterin-thymidine (HAT medium) and resistance to azaguanine [Milstein and Cuello, *Nature*, 305:537–540 (1983)]. The fused hybridomas are capable of synthesizing two different heavy chains and two different light chains, so that theoretically there are ten different combinations which can be formed to produce an antibody containing two heavy chains associated with two light chains.

However, only one of these antibodies will be bifunctional and must be purified from the other forms. The bifunctional antibody will form an even smaller proportion of the total antibodies if the heavy chains are of different isotypes. A disadvantage of this method is that fused hybridomas are less stable cytogenically than the parent hybridomas and non-fused cells.

These first bifunctional antibodies were used as an alternative to indirect immunocytochemistry, since they avoid the need for direct conjugation of an indicator molecule to the antibody by chemical modification which results in a partial loss of activity and increased danger of nonspecific binding.

Another method for producing bifunctional antibodies has been described using heterobifunctional crosslinkers to chemically link two different monoclonal antibodies, so the aggregate will bind to two different targets [Staerz et al, *Nature:* 314:628–631 (1985); Perez et al, *Nature:* 316:354–356 (1985)]. This type of bifunctional antibody has been produced to focus a T-cell response to a chosen target such as a tumor cell or a virally infected cell [Clark and Waldmann, *JNCI,* 79:1393–1401 (1987); Gilliland et al, *Proc. Natl. Acad. Sci. USA*, 85:7719–7723 (1988); Staerz et al, *Eur. J. Immunol.*, 17:571–574 (1987)]. A disadvantage of this type of bifunctional antibody is that the chemical heteroconjugates diffuse slowly into tissues and are rapidly removed from the circulation.

Bifunctional antibodies have also been produced by gene transfer into a hybridoma by retrovirus-derived shuttle vectors or selectable plasmids containing light and heavy chain genes [DeMonte et al, *Proc. Natl. Acad. Sci., USA*, 87:2941–2945 (1990); Lenz and Weidle, *Gene:* 87:213–218 (1990)]. This method produces a mixture of antibodies from which the bifunctional antibody must be purified. However, these transfected hybridomas are more likely to be stable than fused hybridomas.

Bifunctional antibodies can also be produced by reduction of monoclonal antibodies to the single heavy chain associated with its single light chain (HL form), mixing with a second monoclonal antibody followed by reoxidation to produce mixed antibodies [Staerz and Bevan, *Proc. Natl. Acad. Sci., USA*, 83:1453–1457 (1986)].

Bifunctional antibodies produced as described above have been employed in a variety of ways. For example, a bifunctional antibody with binding sites for a tumor cell surface antigen and for a T-cell surface receptor, T3 or Ti, will direct the lysis of specific tumor cells by T cells [Clark and Waldman, *JNCI*, cited above]. A bifunctional antibody with specificity for fibrin and a plasminogen activator has been proposed as capable of increasing the effective concentration of the plasminogen activator in the proximity of a fibrin deposit [Haber et al, *Science*, 243:51–56 (1989)]. More recently, bifunctional antibodies which are specific for gliomas and the CD3 epitope on T cells have been successfully used in treating brain tumors in human patients [T. Nitta et al, *Lancet*, 355:368–371 (1990)].

There remains a need in the art for a method of making recombinant antibodies, particularly bifunctional antibodies which does not require extensive purification steps or chemically controlled conditions.

SUMMARY OF THE INVENTION

This invention relates to novel bifunctional antibodies and a method of making them. As one aspect the present invention provides a bifunctional antibody comprising a first selected Fab component from a first antibody characterized by a modification in its heavy chain constant region and a second selected Fab component from a second antibody characterized by a complementary modification in its heavy chain constant region. The two selected antibody Fab components are preferably derived from different antibodies. The heavy chain constant regions of these Fab components are modified to replace those areas which bring a Fab into association with another Fab to form a complete antigen-binding antibody molecule with complementary "interactive" domains. In a presently preferred embodiment, the interactive domains are reciprocal leucine zipper molecules. In another embodiment, the complementary interactive domains are, a series of positively charged amino acids, e.g. a series of lysine residues, and a series of negatively charged amino acid residues, e.g. a series of glutamic acid residues.

In another aspect, a recombinant antibody of the present invention may be associated with one or more detectable labels.

Yet another aspect of this invention provides a method for producing the recombinant antibodies described above comprising replacing a portion of the heavy chain constant region of a first selected Fab component with a first complementary interactive domain; replacing a portion of the heavy chain constant region of a second selected Fab component with a second complementary interactive domain which will bind strongly to the first domain; and permitting the two modified Fab components to associate. The first and second interactive domains bring the first and second Fab components into proximity to form a single stable antibody construct. Recombinant techniques are employed to associate the first and second interactive domains with the first and second Fab components.

In still another aspect, the present invention provides a method of using the recombinant antibodies of the present invention as a diagnostic agent.

Yet a further aspect of the present invention provides a method of using the bifunctional antibodies as therapeutic agents for the treatment of cancers and virally infected cells.

Other aspects and advantages of the present invention are described further in the following detailed description of preferred embodiments of the present invention.

DETAILED DESCRIPTION OF THE INVENTION

The present invention provides novel recombinant antibodies and a method of making them, which avoid the problems associated with known bifunctional antibodies. Unlike other recombinant bifunctional antibodies and methods for making them, the antibodies and methods of this invention do not require extensive purification or strictly controlled chemical conditions.

According to this invention, a bifunctional antibody or immunoglobulin molecule is obtained by modifying the constant regions of the immunoglobulin heavy chains of two selected antibody Fab fragments by replacing a portion of each heavy chain with a selected "complementary interactive domain". The heavy chains of an antibody molecule are ordinarily responsible for the dimeric nature of an antibody, because they hold the two Fab molecules (the antigen binding portions) of the antibody together.

In the present invention, a portion of the heavy chain of each selected Fab fragment is replaced by a complementary interactive domain. The interactive domains thereby are associated with a selected Fab component and hold together two Fab components in a single molecule. The method and compositions of this invention permit Fab fragments from two different antibodies to be coupled in a single antibody construct, the bifunctional antibody construct.

A Fab component is a portion of a selected immunoglobulin or antibody which contains one site for binding antigen. Each Fab fragment consists of one complete light chain and about one half of the heavy chain (the "$F_d$" piece) of the original antibody, held together by a single disulfide bridge and noncovalent interactions. The "heavy chain" refers to the larger of the two polypeptide chains found in an immunoglobulin, which consists of one variable (V) domain, about three or four constant ($C^H$) domains, a carboxy-terminal segment, and a hinge region. The $F_d$ piece of the heavy chain consists of the $V^H$, $C^H1$, and part of the hinge region. The "hinge region" lies between the heavy chain constant domains $C^H1$ and $C^H2$, and imparts flexibility to the immunoglobulin molecule.

The bifunctional antibody of this invention provides for any two Fab molecules from selected monoclonal antibodies to be employed in the construct. Depending on the use to which the antibody construct will be put, one Fab molecule can be capable of binding a "target antigen", e.g., a tumor cell surface antigen, or a protein. The target antigen can be any antigen which is desired to be measured, detected or treated. The second Fab molecule of the construct of this invention may be an "effector antigen", e.g., a cytotoxic T cell surface antigen, a detectable label, or a therapeutic agent. The effector antigen is generally an antigen which achieves a desired effect in proximity to the target. A detectable label can be used to reveal the presence or level of the target antigen. A therapeutic agent can be used to neutralize the target antigen. A toxin, e.g., ricin, or a cytotoxic T cell can be used to lyse the target when the bifunctional antibody brings the target and effector together.

Alternatively, the recombinant antibody of this invention may comprise the Fab molecules of two monoclonal antibodies directed to different epitopes located on the same cell or on different cells, or directed to antigenic determinants of the same antigen. In this manner, the recombinant antibody of the invention may be used to achieve enhanced antigen-binding ability, Additionally, if one of the Fab molecules of the antibody is directed against an epitope which, although overexpressed in tumor cells, is also present in normal cells, the use of a bifunctional antibody of this invention which also binds a second epitope which is present solely on the tumor cell (or is present in closer proximity to the first epitope on the tumor cell than on normal cells), offers greater specificity than the corresponding monoclonal antibodies from which the recombinant antibody is derived.

The selection of the Fab fragments, or the monoclonal antibody contributing either the particular target or effector Fab components is within the abilities of one of skill in the art given this disclosure. Thus the identity of the Fab fragments of the bifunctional antibodies of this invention is not a limiting factor in this invention.

A "complementary interactive domain" may be defined as a peptide or polypeptide not naturally associated with a Fab component, but which is capable of binding strongly to a complementary interactive domain to hold two selected Fabs in a stable configuration mimicking that of a natural antibody. Each interactive domain is also characterized by an inability to bind stably to itself. However, it will bind strongly to a complementary interactive domain inserted within a portion of a second heavy chain constant region of a second Fab. These domains may be any interactive components which upon mixture associate only with each other. Thus, a novel, facile way of creating recombinant, and particularly bifunctional antibodies, is provided.

A presently preferred complementary interactive domain pair is selected from among known leucine zippers. A leucine zipper is a amino acid sequence found in DNA binding proteins [Busch et al, *Trends in Genetics*, 6:36–40 (1990)], in which every seventh amino acid is leucine (Leu) so that they align down one face of an α-helix and interdigitate upon dimer formation. These sequences thus form a hydrophobic region between the α helices. The leucine zipper regions of the rat oncogenes, c-los and c-jun, can be used in the present invention. When the zipper regions of these two oncogenes come into association, they attract one another and fit together so that the leucines form a hydrophobic zone between the two helices, hence the term 'zipper'. These two regions bind to each other strongly; however c-fos does not interact with itself and c-jun interacts with itself only weakly. Previously, leucine zippers have been used in the study of transcription activating factors [Gentz et al, *Science*, 243:1695–1699 (1989)].

Alternatively, other lock and key interactive domain structures can be used in place of the leucine zipper. For example, an amino acid sequence, e.g., polyglutamic acid, which bears a negative charge, and another amino acid sequence, e.g., polylysine, which bears a positive charge, can be used to replace the heavy chain constant regions in the recombinant antibodies of this invention. Like the leucine zipper sequences, a polyglutamic acid domain associated with a first Fab molecule capable of binding one antigen would bind to a polylysine sequence associated with a second Fab molecule capable of binding a different antigen, due to the charge attraction between the domains. Because of the charge repulsion, neither domain will bind to itself.

Other alternatives may also be selected as complementary interactive domain structures, such as any strongly interactive proteins.

The interactive domain structures in the bifunctional antibodies of this invention may replace all or a portion of the heavy chain constant regions. In a preferred embodiment of this recombinant bispecific antibody, the first and second complementary interactive domains completely replace a portion of the hinge region, and the CH2 and CH3 domains of the heavy chain constant regions of the naturally occurring antibodies. In other words, the selected Fabs are each associated directly with a complementary interactive domain. The two domains interact with each other so as to bring the first and second Fabs into association to create an antibody capable of binding two separate antigens through its two different Fab components.

Even though the hinge region of the Fab is not intact, the modification to the hinge region which occurs upon association with the interactive domain nevertheless permits the hinge region to retain sufficient flexibility to permit each Fab to bind to an epitope on a separate cell or target. See Example 7 which indicates the retention of the hinge flexibility of these constructs.

Also as described in the following examples, a short linking peptide may be optionally inserted between the hinge region and the interactive domain during the construction of the modified Fabs of this invention. The size and composition of the linking peptide may be altered, as desired. For example, the peptide may be increased in size to obtain greater hinge flexibility, if desired. This type of modification to the antibodies of this invention is within the knowledge and abilities of one of skill in the art. The antibodies of this invention are not limited therefore to the presence, composition or size of the linking peptide.

Still another modification of the antibodies of this invention includes inserting the complementary interactive domains between the Fab fragment and another portion of the heavy chain. For example, one or both of the $C^H1$ or $C^H2$ regions of the heavy chain may be added to the end of the selected interactive domain, to create another embodiment of the antibodies of this invention. The addition of these portions of the heavy chain may be performed utilizing the same recombinant DNA techniques described herein and in the following examples.

The stability of the recombinant antibody depends on the binding association of the complementary interacting domains, e.g., the leucine zippers of c-fos and c-jun. However, the stability of the dimeric Fab may be further increased, if desired, by introducing cysteine residues into complementary positions of the interacting domain, e.g., the c-fos and c-jun leucine zippers, so that when the two Fabs associate, the cysteines form a —S—S— bridge upon oxidation. By introduction at complementary positions in the sequence of the interactive domains, no disulfide bridges will form upon homodimer interaction, e.g., the c-fos with the c-fos. This change may be achieved by conventional site directed mutagenesis of the sequence encoding the two leucine zippers. Such enhanced stability may be desirable for therapeutic use of the antibody of this invention.

According to this invention, therefore, a recombinant antibody of this invention may be constructed using various recombinant genetic engineering techniques known to those of skill in the art. See, e.g., Sambrook et al, "Molecular Cloning. A Laboratory Manual." 2nd edition, Cold Spring Harbor Laboratory, Cold Spring Harbor, N.Y. (1989). According to one embodiment of the present invention, for example, recombinant antibody fragments, both Fab fragments and complementary interactive domain fragments are constructed and expressed by essentially following the methods of W. D. Huse et al, *Science*, 246:1275–1281 (1988), which describe the use of several specific oligonucleotides to amplify the light and heavy chain mRNAs. Total RNA, isolated from mouse spleen or in this case hybridoma cells, is used as a template for AMV reverse transcriptase using specific oligonucleotides as primers to initiate cDNA synthesis on the light or heavy chain mRNAs. In the next step, PCR is performed on aliquots of the reverse transcriptase reaction using different oligonucleotides, which show homology to different heavy chain families of genes and are defined by Huse et al. Those reactions that showed a 700 bp band are purified by gel electrophoresis after digestion with restriction enzymes, and the fragment ligated to pMN1 fos or jun. This light chain is cloned in a similar way. Conventional chemical synthesis methods may also be used in addition to genetic engineering methods in some instances.

Briefly, as described in detail in Example 1 below, an embodiment of the present invention having two Fab fragments joined by a leucine zipper is prepared as follows. Plasmids containing the sequences for a desired light chain of a selected antibody and a desired interactive domain, in this case, a leucine zipper sequence, may be constructed in lambda vectors, such as those described by Huse et al, cited above. Other similar known vectors may be employed for this purpose. Desirably, these plasmids or vectors also contain appropriately placed restriction sites to permit the introduction of selected light or kappa (K) chain sequences and the $F_d$ or variable ($V_H$) segment of the heavy chain ($V_H$—$C_{H1}$) of the selected antibody donating the Fab fragment.

The plasmid for the heavy chains preferably contains a sequence encoding a peptide for which a monoclonal antibody is available for subsequent use in immunoaffinity purification of the fused proteins. As described in detail in Example 1, light and heavy chains are separately inserted into a plasmid before being transferred into an expression vector. The heavy chain signal sequence and two or more codons of the heavy chain from a selected monoclonal antibody are amplified and cloned into the plasmid. The same procedure is followed for the light chain.

Following this, rat c-fos leucine zipper DNA [T. Curran et al, *Oncogene*, 2: 79–84 (1987) and rat c-jun leucine zipper DNA [M. Sakai et al, *Cancer Res.*, 49:5633–5637 (1989) are individually amplfied and cloned into separate selected vectors. In the next step, the $V_H$—$C_{H1}$ RNA sequences from the hybridomas which produce the selected antibodies are amplified by PCR using specific oligonucleotides. Similarly the κ RNA sequences are amplified by PCR. Exemplary primers are described by W. D. Huse et al, cited above. The PCR products of one hybridoma are inserted into a set of plasmids, one of which carries the light chain and one of which carries the heavy chain. The products of a second hybridoma are inserted into a similar second set of plasmids. These inserts are then excised from their respective plasmids, the ends filled in, and then ligated into a selected plasmid, which will then contain either the light or heavy chain of a selected hybridoma. The plasmid containing the heavy chain also contains the complementary interacting domain insert.

The resulting plasmids encoding the light chain and heavy chain/leucine zipper regions for a selected hybridoma are co-transfected into a selected host cell, e.g., a mouse myeloma Sp2/0 cell or a human U293 cells, and selected by use of the selection marker. Cultures are grown to late log phase and induced if desired, e.g., by isopropyl thiogalactoside (IPTG) for bacterial cells, harvested and resuspended in water to release the Fab from the periplasmic space by osmotic shock.

This method results in the production of a Fab fragment with a leucine zipper tail. This same strategy may be readily repeated using the second set of plasmids for the second hybridoma to produce the second Fab fragment with the leucine zipper tail corresponding to the first Fab-leucine zipper fragment.

The first Fab-domain fragment is collected from culture media, and may preferably be purified and concentrated by immunoaffinity chromatography and is mixed with the second Fab-domain fragment which is similarly in solution. This mixture of solutions results in the two interacting domains, e.g., the reciprocal leucine zippers, becoming associated and the formation of a recombinant antibody construct.

The resulting recombinant antibody is tested for its ability to target the desired antigen or antigens and for the ability of the effector Fab domain to generate the expected effect. In the case of a bifunctional antibody which has Fab molecules directed against a tumor cell antigen and a T cell epitope, this activity can be measured in contrast to the original target and effector antibodies. For example, it is expected that the individual Fabs would not direct the desired effect on the target cells, while the mixture of the two Fabs will have the desired effect, e.g., lysis, on the target cells, but no effect on unrelated cells.

In the case of a recombinant antibody which has Fab molecules directed against two antigens on a single tumor cell, this activity can be measured in contrast to the original antibodies. It is expected that the recombinant antibody of the invention will have an enhanced, more specific, binding effect on the target tumor cells as compared to binding achieved by monoclonal antibodies from which the recombinant antibody Fab molecules are derived.

The description of the above embodiment of this invention may readily be adapted to the use of other embodiments, such as the polyGlutamic Acid/polyLysine sequences, in place of the leucine zipper sequences. One embodiment of the use of this alternative complementary interactive domain is illustrated in Example 4 below.

Expression systems, including selected host cells and appropriate expression vectors, suitable for construction and expression of the Fab fragments and the entire recombinant antibody include known bacteria, yeast, insect and mammalian cell expression systems. Mammalian expression systems, including a mouse myeloma expression system, among other known mammalian systems are presently preferred. However, bacterial expression systems, particularly E. coli expression systems, may also be desirable. The only requirements for the suitable vector and host cells employed in this method are an efficient, preferably inducible promoter, a 5' untranslated region with a ribosome binding site for E. coli (if bacterial expression is employed), or a consensus initiation signal for eukaryotes, a signal sequence for secretion, a sequence containing suitable restriction sites for inserting the PCR product, a sequence encoding an excisable intron for animal cells, but not for yeast; a poly A addition site for eukaryotic cells, and selectable marker suitable for the host cell. A second vector is required for eukaryotic cells containing all of the above features but with a different selectable marker. The host cell may be any cell capable of high levels of protein secretion. The selection of such expression systems and the components thereof are well within the skill of the art.

The recombinant antibody produced according to present invention may be used as a diagnostic agent to detect qualitatively or quantitatively the presence of a selected target antigen in a biological sample. This antibody may be employed in various tissue culture diagnostic assays known to those of skill in the art. The recombinant antibody for such use may be provided with one or more detectable labels. The first antigen binding site and the second antigen binding site of the antibody may each bear a detectable label. The label may be one which is capable of visual detection or may be selected from systems detectable by other means, including, for example, fluorescent compounds, radioactive compounds or elements or immunoelectrodes. These and other appropriate conventional label systems are known to those of skill in the art.

Additionally, the recombinant antibody produced by the method of this invention may be used in therapeutic regimens, such as the treatment of cancers. For example, a bifunctional antibody having a binding site for a tumor cell surface antigen and for a T-cell surface receptor would be administered, by in vivo or ex vivo therapy, so that lysis of the tumor cells by T cells is enhanced. It is expected that the bifunctional Fab is sufficiently stable to demonstrate its ability to achieve the effect, e.g., directed lysis of tumor cells by T cell clones or enhanced, specific binding of tumor cells.

Alternatively the second Fab fragment could bind a biological toxin, e.g., ricin, so that the toxin would be delivered to the site of the tumor cell by the binding action of the first Fab fragment of the bifunctional antibody. Similar therapeutic or diagnostic functions could be developed using these antibodies with other biological targets in mind.

In addition, a recombinant antibody of the invention may be used to form an antibody conjugate by fusing toxins, radioisotope binding domains, enzymes capable of converting prodrugs to drugs, and other nucleotide sequences to the complementary interactive domains of this invention, or to other portions of the antibody of this invention. For example, an antibody of this invention may be provided with enhanced tumor cell killing ability by attaching a known T cell binding site to the end of the leucine zipper, using conventional recombinant methods known to the art, and described herein.

Thus, a recombinant antibody of the invention may comprise Fab molecules of two different antigens of the same tumor cells, a complementary interacting domain (e.g., leucine zipper construct) which keeps the Fab components in close association, and a T cell binding site. Such a recombinant antibody could achieve enhanced specific tumor cell binding and direct lysis of the tumor cell by binding a T cell.

In another embodiment, the recombinant antibody of this invention may be further modified by attaching a gene encoding a cytokine, preferably a lymphokine, to the lower end of the interactive domain construct. Suitable cytokines are well known to those of skill in the art and include, among others, the interleukins (IL) 1 through 9, the interferons and tumor necrosis factor (TNF). Attachment of the sequences encoding such proteins to the antibody constructs may be performed using the conventional techniques described below in the examples.

The following examples are provided to illustrate aspects of the invention only. The examples use ME361, human melanoma specific antibody [described in Herlyn et al, *JNCI*, 74:283–289 (1985) and Herlyn et al, *Cancer Res.*, 45:5670–5676 (1985), available from the American Type Culture Collection (ATCC HB9235), 12301 Parklawn Drive, Rockville, Md. 20852], as the target Fab and OKT3, an antibody specific for CD3 [available from the ATCC (ATCC CRL 8001)], a T cell antigen, as the effector Fab for purposes of illustration only. These examples are not intended to limit the scope of this invention.

EXAMPLE 1

Construction of Vectors for the Heavy Chain Containing a Leucine Zipper

A. Preparation of Multicloning Site Plasmid

A novel multicloning site plasmid, made as follows, facilitates the assembly of light and heavy chain cDNAs. Complementary oligonucleotides were synthesized to contain the following restriction sites in the following order: from the 5' end: EcoRI, XmaI, BamHI, XbaI, SpeI, SacI, SalI, XbaI, BglII, XmaI, and HindIII. The oligonucleotides, after annealing, were cut with EcoRI and HindIII and ligated to pUC18 [Bethesda Research Labs; Norrander et al, *Gene*, 20:101–106 (1983)] cut with the same enzymes. The plasmid containing the above restriction enzyme sites is referred to as pMNI.

B. Assembly of Heavy Chain Gene pMNI

The heavy chain gene is assembled in pMNI before being transferred to an expression vector. The heavy chain signal sequence and the first four codons of the mature heavy chain for mAb 17-1A [Sun et al, *Proc. Natl. Acad. Sci. USA*, 83:214–218 (1987)] is amplified by the PCR reaction using a 5' primer (5' 17-1A HSS) containing a BglII restriction site and 3' primer (3' 17-1A HSS) containing a SalI restriction site which changes the codons for the 5th and 6th amino acids from CAG CAG to GTC GAC. These primers are identified in Table 1 below. The product is digested with BglII and SalI and is cloned into the BglII to SalI site of pMNI, resulting in pMNI-HI.

TABLE 1

| Oligonucleotide Primers | |
|---|---|
| 5' 17-1A HSS | GGAGATCTCACCATGGAATGGAGCAGA |
| 3' 17-1A HSS | GGGTCGACCAACTGGACCTGGGAGTG |

C. Cloning of Peptide Into Heavy Chain Gene

In addition to the leucine zipper, a sequence encoding a peptide for which a monoclonal antibody is available is optionally cloned into the heavy chain gene so that the monoclonal antibody can be used for immunoaffinity of the fused proteins. For this purpose, a plasmid was rescued from the lambda vector λHc2, which is derived from λzap, as described by Huse et al, cited above, by inserting into the multicloning site a ribosome binding site, a leader sequence from the gene pelB to facilitate secretion in *E. coli*, XhoI and SpeI restriction sites, DNA encoding a decapeptide and a stop codon. λzap, whose construction is described by J. M. Short et al, *Nucl. Acids Res.*, 16:7583–7600 (1987), contains the Bluescript SK phagemid derived from pUC19 with a colE1 origin of replication, a resistance gene and an initiator and terminator sequence from the f1 phage origin of replication. With these sequences present, it is possible to recover the Bluescript phagemid as a plasmid when λzap is co-infected with a f1 helper phage, [Short et al, cited above]. In the same way, pHc2 is obtained from λHc2. DNA encoding a decapeptide, YPYDVPDYA, was cloned into λHc2 and therefor pHc2, to provide a peptide tag which will be present on the heavy chain, after the SpeI site. The decapeptide is derived from the amino acid sequence of flu hemagglutinin, peptide HAI. The monoclonal antibody, 12CA5, described by J. Field et al, *Mol. Cell Biol.*, 8:2159 (1988), was raised against the peptide HAI, and therefore can be used to purify Fab fragments containing the decapeptide.

The rat c-fos leucine zipper DNA was prepared by PCR amplification using the primers 5' fosLZ and 3' fosLZ shown in Table 2 below. The 5' fosLZ primer encodes from the 5' end, an SpeI site, codons for three glycine residues to act as a spacer, followed by codons for the leucine zipper. The 3' primer contains an XbaI site which is compatible with SpeI. The product was digested with SpeI and XbaI and ligated to the plasmid pHc2 digested with SpeI.

TABLE 2

| Primers | |
|---|---|
| 5' fosLZ | GGACTAGTGGTGGCGGTGAGCTGACAGATACGCTCCAAG |
| 3' fosLZ | GGTCTAGAGGCTGCCAAAATAAACTCCAG |

After screening to detect colonies containing the c-fos leucine zipper, the DNA was sequenced to identify those samples that had the leucine zipper ligated in the correct orientation so that an SpeI site was retained at the 5' end of the leucine zipper. This plasmid is called pHc2/fosLZ.

The cloning and sequence of rat c-jun CDNA, including its leucine zipper DNA has been described [M. Sakai et al, *Cancer Res.*, 49:5633–5637 (1989)]. Using the same procedures described above, rat c-jun leucine zipper DNA was amplified using primers 5' junLZ and 3'junLZ (Table 3) and cloned to give pHc2/junLZ.

TABLE 3

| Primers | |
|---|---|
| 5' junLZ | GGACTAGTGGTGGCGGTGAGCGGATCGCCCGG |
| 3' junLZ | GGTCTAGAGTTCATGACTTTCTGTTTAAG |

From pHc2/fosLZ and pHc2/junLZ the sequence encoding the leucine zipper and the decapeptide is excised by SpeI and EcoRI, and then is cloned into pMNI-H1 (containing the signal sequence) to give pMNI-H2 fos and pMNI-H2 jun.

D. Synthesis and Cloning of the $V_H$-$C_{H1}$ DNA

In general, the heavy chain primers [W. D. Huse et al, cited above] are used to amplify the $V_H$-$C_{H1}$ DNA. However, for this example, the hybridomas ME361 and OKT3 produce a γ2a heavy chain, and the nucleotide sequence contains an XhoI site [P. Schreirer et al, Proc. Natl. Acad. Sci. USA, 78:4495–4499 (1981)], so that the PCR product is cut by XhoI and the $V_H$-$C_{H1}$ DNA cannot be cloned.

ME361 [J. Thurin et al, Cancer Res., 47:1229–1233 (1987)] is a hybridoma which secretes an antibody showing specificity for glycolipids abundant on human melanoma cells. OKT3 [E. Reinherz et al, Cell, 19:821–827 (1980)] is a hybridoma secreting an antibody specific for CD3 found on T cells. Therefore, a corresponding set of 5' primers were synthesized using the sequence GTC GAC, the recognition site for SalI, in place of CTC GAG, the recognition site for XhoI. In addition, the following, different 3' primer was made for γ2a:

3' $Y^{2a}$ CTTACTAGTGGGCCCTCTGGGCTCAAT

Using these primers, the $V_H$-$C_{H1}$ region was amplified from total RNA from hybridomas ME361 and OKT3.

The amplified material after digestion with SalI and SpeI was cloned into pMNI-H2 fos and pMNI-H2 jun digested with SalI and SpeI to give pMNI-H2 fos/ME361 $V_H$-$C_{H1}$ and pMNI-H2 jun/OKT3 $V_H$-$C_{H1}$.

EXAMPLE 2

Construction of Vectors for the Light Chain

A. Assembly of Light Chain Gene in pMNI

The light chain signal sequence and the first two codons of the mature light chain of mAb 17-1A is amplified by the PCR reaction using a 5' primer (5' 17-1A KSS) containing a BamHI at its 5' end and a 3' primer (3' 17-1A KSS) containing a SacI site which changes the codons for the 1st and 2nd codons of the mature 17-1A from AAC AAT to GAG CTC as well as the two codons preceding these codons from GAT GGG to AGA TGT to maintain an amino acid sequence appropriate for cleavage.

TABLE 4

Oligonucleotide Primers

| | |
|---|---|
| 5' 17-1A KSS | GGGGATCCAAGATGGAATCACAGACTCTGG |
| 3' 17-1A KSS | GGGAGCTCACATCTGGCTCCATATAACCAGAGCAGTATGG |

The amplified product after digestion with BamHI and SacI is cloned into the BamHI to the SacI site of pMNI to give pMNI-L1.

B. Synthesis and Cloning of κDNA

Using the light chain primers described in W. D. Huse et al (cited above) the κ chains were amplified using the polymerase chain reaction from total RNA extracted from the hybridomas ME361 (anti-target) and OKT3 (the anti-effector). The amplified material after digestion with SacI and XbaI was cloned into pMNI-L1 digested with the same two enzymes. The plasmids obtained are called pMNI-L1/ME361 and pMNI-L1/OKT3.

EXAMPLE 3

Expression System for Production of the Bifunctional Antibody

A. Cloning into an Expression Vector

A variety of expression vectors suitable for expression of the recombinant proteins in different animal cells may be used for the production of the antibody of this invention. In this example, pHEKneo [Hendricks et al, Gene, 64:43–51 (1988)] for expression in mammalian mouse myeloma Sp2/0 cells. The plasmid pHEKneo is modified by removing the neo gene and replacing it with the gpt gene by blunt-end ligation to produce plasmid pHEKgpt.

The light chain and heavy chain fused genes for ME361 are excised from the appropriate pMN plasmid described in the examples above by EcoRI and HindIII, and the ends are filled in with DNA polymerase (Klenow fragment). This ligation is performed by digesting both pHEKneo and pHEKgpt with XhoI, and filling the ends in as above. The blunt ended heavy chain fused gene is ligated to linearized pHEKneo, and the light chain ligated to linearized pHEKgpt, resulting in the expression vectors, pHEKneo HfosLZ/ME361 and pHEKgpt L/ME361.

In a similar manner the light and heavy chain fused genes for OKT3 are cloned into pHEKneo and pHEKgpt. Plasmids containing the inserts in the correct orientation are identified by restriction enzyme digestion.

B. Expression and Purification of Fabs

The plasmids pHEKneo HfosLZ/ME361 and pHEKgpt L/ME361 are co-transfected into mouse myeloma Sp2/0 cells by electroporation. After 48 hours, the cells are grown in the presence of the antibiotic G418 and mycophenolic acid. Resistant colonies are checked for expression of a Fab capable of binding specifically to human melanoma cells.

In a similar manner the plasmids containing OKT3 H and L sequences are transfected into mouse myeloma Sp2/0 cells. Approximately 1–20 μg Ab/mL of medium can be produced in this way.

The supernatants containing ME361 Fab and OKT3 Fab were subjected to immunoaffinity chromatography using the monoclonal antibody 12CA5 [Wistar Institute, Philadelphia, Pa.] attached to the column which binds the decapeptide on the tail of the heavy chain. From the column, the Fabs were eluted in a concentrated form. Alternatively a polyclonal antibody against c-fos and c-jun may also be employed in this purification step.

To construct the bifunctional antibody from these Fab-domain fragments, the first Fab-domain fragment is mixed with the second Fab-domain fragment which is similarly in solution, resulting in the reciprocal leucine zippers becoming associated. The two Fabs, Fab ME361/fosLZ and Fab OKT3/junLZ were mixed together at approximately 0.5 mg/ml to form a bifunctional antibody. The resulting bifunctional antibody is characterized by the first Fab (ME361) as a binding site for the human melanoma antigen and the second Fab (OKT3) as a binding site for the CD3 T cell antigen.

The bifunctional antibody will be tested for its ability to target CD3 positive T cell clones for lysis of the melanoma cell using the standard chromium-51 release assay to measure cell lysis, as described by Perez et al, *Nature,* 316:354–356 (1985); Staerz et al, *Proc. Natl. Acad. Sci. USA,* 83:1453–1457 (1986); Gilliland et al, *Proc. Natl. Acad. Sci. USA,* 85:7719–7723 (1988). In this assay, target cells, such as human melanoma cells, are preincubated with chromium-51. Any chromium-51 not taken up by the cells will be removed by washing. Labeled cells are incubated for 4 hours with cloned T cells in the presence or absence of bispecific antibody. The release of chromium-51 into the medium is measured, as an indication of cell lysis. Thus, it is expected that the individual Fabs would not direct lysis of the melanoma cells, while the mixture of the two Fabs will result in lysis of the melanoma cells but not an unrelated tumor cell.

EXAMPLE 4

Alternative Method of Cloning Into Expression Vector

As an alternative to part A of Example 3, the pMN1 inserts are excised with EcoRI and HindIII, the ends filled in with DNA polymerase (Klenow fragment) and ligated into pCDM8 [B. Seed, *Nature,* 329:840–842 (1987)] cut with BstE1 and the ends filled in. Constructs are checked for the correct orientation.

Plasmids pCDMS-L1/ME361 and pCDM8-H2/fos/ME361 are cotransfected into human U293 cells using DEAE-dextran and chloroquine [B. Seed et al, *Proc. Natl. Acad. Sci. USA,* 84:3365–3369 (1987)]. After 24 hours, the cells are grown in a synthetic medium [ITS, Hybritech] which does not contain any gamma globulin. The medium is harvested for 3–4 days.

In the same way the light and heavy chains for OKT3 are produced. About 100–200 ng Ab/ml medium can be produced.

EXAMPLE 5

Expressing Bifunctional Antibodies in *E. Coli*

This example provides an alternative method to that of Example 1 for producing the antibodies of the invention.

A. Construction of Vectors for the Heavy Chain Containing a Leucine Zipper

Using the methods described in Huse et al, cited above, plasmids were rescued from the two lambda vectors λLc1 and Hc2 [Huse et al, cited above] with a f1 helper phage [Short et al, (1988) cited above]. The plasmids are termed pLc1 (for K chains) and pHc2 (as described in Example 1) for heavy chains. These plasmids also contain appropriately placed restriction sites to permit the introduction of light or kappa (K) chain sequences and the $F_d$ segment of the heavy chain ($V_H$-$C_{H1}$) of the selected antibody donating the Fab fragments.

The plasmids pHc2/fosLZ and pHC2/jun LZ were produced as described in Example 1.

B. Synthesis and Cloning of κDNA

Using the light chain primers listed by W. D. Huse et al, cited above, the K chains were amplified using the polymerase chain reaction from total RNA extracted from the hybridomas ME361 (anti-target) and OKT3 (the anti-effector). The amplified material after digestion with SacI and XbaI was cloned into pLc1 digested with the same two enzymes. The plasmids obtained are called pLc1-ME361K and pLc1-OKT3K. For each hybridoma the K sequence is excised from pLc1 and ligated into the corresponding pHc2/fosLZ and pHc2/junLZ so that both the K and $V_H$-$C_{H1}$ sequences form a bicistron with the lacZ promoter.

C. Synthesis and Cloning of the $V_H$-$C_{H1}$ DNA

Using the same procedures described in Example 1, including the γ2a primer, the $V_H$-$C_{H1}$ region was amplified from total RNA from hybridomas ME361 and OKT3. The amplified material after digestion with SalI and SpeI was cloned into pHc2/fosLZ and pHc2/junLZ digested with XhoI and SpeI to give pHc2/fosLZ/ME361 $V_H$-$C_{H1}$ and pHc2/junLZ/OKT3 $V_H$-$C_{H1}$.

D. Construction of Plasmids Containing K and $V_H$-$C_{H1}$ DNA

The K chain DNA was excised from pLc1/ME361K by digestion with EcoRI and KpnI, and the K chain DNA was force cloned into pHc2/fosLZ/ME361 $V_H$-$C_{H1}$ which had been digested with EcoRI and KpnI. Similarly, the OKT3 K chain DNA was cloned into pHc2/junLZ/OKT3 $V_H$-$C_{H1}$. These two plasmids were transfected into a bacterial host cell, *E. coli* JM105, or any strain which overproduces the lac repressor.

E. Expression and Purification of Fabs

The transformed cells were grown in hybrid culture from mid to late log phase when IPTG (to 1 mM) was added to induce expression of the lac Z promoter. After 2–6 hours of induction, the cells were selected for ampicillin resistance, harvested by centrifugation, resuspended in a buffered sucrose solution and subjected to mild osmotic shock by dilution with 4 volumes water to release the Fab from the periplasmic space. After 30 minutes on ice, the suspension was centrifuged [Pluckthun et al, *Methods of Enzymology,* 178:497–515 (1989)].

The supernatant was subjected to immunoaffinity chromatography using the monoclonal antibody 12CA5 [Wistar Institute, Philadephia, Pa.] attached to the column which binds the decapeptide on the tail of the heavy chain. From the column, the Fabs were eluted in a concentrated form.

The two Fabs, Fab ME361/fosLZ and Fab OKT3/junLZ, were mixed together at approximately 0.5 mg/ml to form a bifunctional antibody.

EXAMPLE 6

Method of Constructing Bifunctional Antibodies with POLYGLU/POLYLYS Interactive Domain This examples provides an illustration of another interactive domain useful in constructing bifunctional antibodies of this invention.

DNA encoding polyglutamic acid is synthesized as an oligonucleotide with, at the 5' end, the nucleotide sequence for the restriction enzyme SpeI, ACTAGT, followed by the codons for three glycine residues (GGN) to act as a spacer, followed by the codons for 10 glutamic acid residues (GAA/GAG). The number of glutamic acid residues is not critical, but should be sufficient to form a strong interaction with polylysines via salt bridges. The glutamic acid residues can be interspersed with codons for small neutral amino acids, such as alanine and serine.

A sequence complementary to the polyGlu sequence is synthesized with the nucleotide sequence of the restriction enzyme XbaI, TCTAGA, at its 5; end, followed by nucleotides complementary to those encoding glutamic acid, followed by those for glycine.

These two oligonucleotides are annealed and then ligated to pHcI cut with SpeI (which joins the polyGlu sequence to DNA encoding a TAG peptide in the plasmid pHc1). Plasmids containing the oligonucleotide are checked to identify those that retain the SpeI site, 5' of the DNA encoding the glutamic acids. From such a plasmid, the DNA encoding glutamic acid and the TAG peptide are excised with SpeI and EcoRI and the fragment ligated to pMN1 containing the heavy chain leader sequence of MaB 17-1A, also cut with SpeI and EcoRI.

The $V_H$ and $C_{H1}$ DNA amplified by PCR from the RNA of hybridoma ME361, as previously described, is cloned into the SalI to SpeI sites of the pMN1 plasmid constructed above.

Plasmid encoding the OKT3 heavy chain linked to polylysine is constructed as described above for ME361, except the codons encoding glutamic acid are replaced by those for lysine, AAA or AAG, and the $V_H+C_{H1}$ DNA for OKT3 are used.

These Fabs containing polyglutamic acid and polylysine may be expressed as follows. The heavy chain DNA constructs are transferred into expression vectors, pCDM8 or pHEk, and co-transfected with their corresponding light chains into mammalian cells, as described for the Fabs containing leucine zippers.

Bifunctional Fabs are formed by mixing of the two different Fabs. The resulting antibodies are tested as described in the examples above.

EXAMPLE 7

Detection of Leucine Zipper Interaction

The following experiments demonstrate that a dimeric Fab forms when a Fab with a c-fos leucine zipper (LZ) is mixed with a Fab with a c-jun LZ.

A. HPLC and SDS-PAGE Analyses

A c-fos LZ/Fab OKT3 alone, and mixed with a c-jun LZ/Fab OKT3, both Fabs made according to Example 1, were applied to a high power liquid chromatography (HPLC) gel filtration column, that had previously been calibrated with proteins of known molecular weights. The elution of Fabs was followed by first concentrating the elution fractions by trichloracetic acid precipitation. The precipitates were redissolved in Laemmli sample buffer before sodium dodecyl sulfate polyacrylamide gel electrophoresis (SDS/PAGE). Proteins were transferred to nitrocellulose and the presence of Fabs was detected by a goat anti-mouse Fab, followed by swine anti-goat IgG conjugated with alkaline phosphatase.

The results of the SDS-PAGE demonstrated that c-fos LZ/Fab OKT3 elutes at approximately 60,000 daltons; while the mixture shows two peaks with approximate weights of 60,000 and 130,000 daltons, which is the expected result if c-fos LZ/Fab OKT3 interacts with c-jun LZ/Fab OKT3.

B. FACS Analysis

The binding of modified OKT3 Fabs prepared according to this invention to normal lymphocytes was determined by FACS analysis using a fluorescein labeled anti-mouse Fab. Conventional FACS analysis was performed using a low concentration of the fluorescein labeled second antibody to obtain a low background of nonspecific binding. The results are reported in Table 5 below.

TABLE 5

| Total (ng) | % Binding of Lymphocytes by OKT3 Fabs | | |
|---|---|---|---|
| | fos LZ/Fab | jun LZ/OKT3 | fosLZ/Fab + jun Lz/Fab |
| 30 | 10.1 | 5.0 | 33.0 |
| 15 | 3.2 | 3.5 | 33.5 |
| 7.5 | 3.8 | 3.6 | 30.1 |

The c-fos LZ/Fab OKT3 and c-jun LZ/Fab OKT3 (prepared as described in the above examples) showed little, if any, binding to normal lymphocytes when analyzed individually. However, when mixed to form a recombinant (homodimeric) antibody, the mixture of the two OKT3 Fabs bound very clearly to the cells. Cells (50,000) mixed with fluoresceinated (FITC) labelled antibody alone gave 4% binding, those mixed with OKT3 antibody gave 85% binding.

In general, an antibody binds 5 to 10 times that of a Fab. The increased binding detected with the mixture of Fabs is the expected result if the Fabs form a dimeric Fab via the leucine zipper construct of this invention. Similarly these results demonstrate that the hinge region of the recombinant antibody construct retains sufficient flexibility to permit the individual Fab fragments to bind in a manner similar to that of normal antibodies. If the hinge region were adversely affected by the modification of the leucine zipper, the rigidity of the Fab antibody binding regions would have reduced the ability of the dimeric recombinant antibody to bind the target.

EXAMPLE 8

Biological Assays

A. Antibody Binding Assays

Binding of the c-fos LZ/Fab ME361 to human melanoma cells WM793 [M. Herlyn et al, *Cancer Res.*, 45:5670 (1985)] is measured by indirect immunofluorescence analysis in the cytofluorograph [Coulter, Inc., Miami, Fla.] using fluoresceinated goat anti-mouse F(ab')$_2$ antibody to detect binding of LZ/Fab ME361 to the melanoma cells. Antibody sensitized cells are incubated first with either Mab 12CA5 specific for the tag decapeptide or rabbit anti-LZ antibody followed by the addition of fluoresceinated goat anti-mouse F(ab')$_2$ or goat anti-rabbit IgG antibody. Colon carcinoma cells SW1116 [H. Koprowski et al, *Somat. Cell Genet.*, 5:957 (1979)] are used as ME361 antigen-negative target cells. C-jun LZ/Fab OKT3 is a negative antibody control. The binding of c-jun LZ/Fab OKT3 to cytotoxic anti-human melanoma T cell clones [R. Somasundaram et al, *AACR Proc.*, 32:245 (1991), abstract 1458] is determined in immunofluorescence analysis similar to those described above.

B. Cytotoxic Assay

Melanoma cells WM793 and colon carcinoma cells SW1116 (negative control) are labeled first with 51Cr, then incubated with different concentrations of the LZ/Fabs of this invention, either singly or in a recombinant antibody. Concentrations may range between about 1 to about 10 μg/ml. Thereafter increasing numbers of effector cells (effector-to-target ratios of between about 5 to about 50) previously activated with 10 U/ml of recombinant IL-2 [ ] are added to the cells. Lysis of cells is the positive result in WM793 cells. Negative results are present in the SW1116 control cells for the ME361 antigen. These results are compared to measure specific antibody-directed killing.

Numerous modifications and variations of the present invention are included in the above-identified specification and are expected to be obvious to one of skill in the art. For example, use of other appropriate mAbs, Fabs, interactive domains and detectable labels are contemplated in the performance of this invention. Such modifications and alterations to the compositions and processes of the present invention are believed to be encompassed in the scope of the claims appended hereto.

What is claimed is:

1. A bispecific antibody comprising:
    a first Fab fragment capable of binding a first antigen comprising a heavy chain constant region comprising a first complementary domain not naturally present in the Fab but capable of stably binding to a second complementary domain but not to itself, and
    a second Fab fragment capable of binding a second antigen comprising a heavy chain constant region comprising a second complementary domain not naturally present in the Fab but capable of stably binding to the first complementary domain but not to itself,
    wherein the first and second complementary domains bind to form a leucine zipper and to stably associate said first Fab fragment and said second Fab fragment into a single antibody construct capable of binding to two antigenic sites.

2. The antibody according to claim 1 comprising a detectable label.

3. The antibody according to claim 1 wherein the first Fab and the second Fab each bear a detectable label.

4. A method for producing a bispecific antibody comprising mixing a modified first Fab capable of binding a first antigenic site, said first Fab comprising a heavy chain constant region comprising a first complementary domain not naturally present in the Fab but capable of binding to a second complementary domain, and a modified second Fab capable of binding a second antigenic site, said second Fab comprising a heavy chain constant region comprising a second complementary domain not naturally present in the Fab but capable of binding to the first complementary domain, each said domain capable of stably binding to the other but not to itself, whereby the first and second complementary domains interact to form a leucine zipper to associate the first and second modified Fab regions into a single antibody construct capable of binding to two antigenic sites.

5. The method according to claim 4 comprising culturing a selected host cell transformed with a DNA molecule comprising the sequence of said first or second modified Fab.

6. The method according to claim 5 wherein the host cell is selected from the group consisting of a bacterial cell, a yeast cell and a mammalian cell.

7. The method according to claim 6 wherein the hose cell is E. coli.

8. The method according to claim 6 wherein the host cell is a mouse myeloma cell.

9. A method for detecting the presence of a selected antigen in a biological sample comprising;
    probing said sample with the bispecific antibody of claim 1, wherein said first or second modified Fab is capable of binding to said selected antigen and wherein said antibody contains a detectable label,
    and assaying for the presence of the label.

10. A bispecific antibody comprising:
    a first Fab fragment capable of binding a first antigen comprising a heavy chain constant region comprising a first complementary domain not naturally present in the Fab but capable of binding to a second complementary domain, and
    a second Fab fragment capable of binding a second antigen comprising a heavy chain constant region comprising a second complementary domain not naturally present in the Fab but capable of binding to the first complementary domain,
    wherein the first and second complementary domains bind to form a leucine zipper and to stably associate said first Fab fragment and said second Fab fragment into a single antibody construct capable of binding to two antigenic sites, wherein said first domain is the leucine zipper region of c-fos oncogene and said second domain is the leucine zipper region of c-jun oncogene.

11. A method for producing a bispecific antibody comprising:
    mixing a modified first Fab capable of binding a first antigenic site comprising a heavy chain constant region comprising a first complementary domain not naturally present in the Fab but capable of binding to a second complementary domain and,
    a modified second Fab capable of binding a second antigenic site comprising a heavy chain constant region comprising a second complementary domain not naturally present in the Fab but capable of binding to the first complementary domain, each said complementary domain capable of stably binding to the other but not to itself,
    whereby the first and second complementary domains interact to form a leucine zipper to associate the first and second modified Fab regions into a single antibody construct capable of binding to two antigenic sites, wherein the complementary domains are selected from the leucine zipper regions of the oncogenes c-fos and c-jun.

* * * * *

UNITED STATES PATENT AND TRADEMARK OFFICE
CERTIFICATE OF CORRECTION

PATENT NO. : 5,582,996
DATED : December 10, 1996
INVENTOR(S) : Peter J. Curtis

It is certified that error appears in the above-indentified patent and that said Letters Patent is hereby corrected as shown below:

Col. 2, line 24, delete "Which" and insert in place thereof -- which --.

Col. 4, line 49, delete "c-los" and insert in place thereof -- c-fos --.

Col. 13, line 30, delete "pCDMS-L1/ME361" and insert in place thereof -- pCDM8-L1/ME361 --.

Signed and Sealed this

Tenth Day of June, 1997

BRUCE LEHMAN

*Attest:*

*Attesting Officer*   Commissioner of Patents and Trademarks